United States Patent
Chaudhary et al.

(10) Patent No.: US 7,061,001 B2
(45) Date of Patent: Jun. 13, 2006

(54) METHOD AND APPARATUS FOR TROUBLESHOOTING PHOTOSENSORS

(75) Inventors: Vishal Chaudhary, New Milford, CT (US); Badi Ebrahimifard, Salt Lake City, UT (US)

(73) Assignee: Pitney Bowes Inc., Stamford, CT (US)

( * ) Notice: Subject to any disclaimer, the term of this patent is extended or adjusted under 35 U.S.C. 154(b) by 390 days.

(21) Appl. No.: 10/608,965

(22) Filed: Jun. 27, 2003

(65) Prior Publication Data

US 2004/0262549 A1    Dec. 30, 2004

(51) Int. Cl.
*H04N 5/335* (2006.01)

(52) U.S. Cl. ................. 250/559.45; 348/246

(58) Field of Classification Search .......... 250/559.45; 348/246, 125, 247
See application file for complete search history.

(56) References Cited

U.S. PATENT DOCUMENTS 5,416,516 A * 5/1995 Kameyama et al. ........ 348/246
6,307,393 B1 * 10/2001 Shimura ..................... 348/246

* cited by examiner

*Primary Examiner*—Stephone B. Allen
(74) *Attorney, Agent, or Firm*—Michael J. Cummings; Steven J. Shapiro; Angelo N. Chaclas (57) ABSTRACT

A method and apparatus for troubleshooting a plurality of photosensors in a machine, such as a mail sorter and mail inserter. The troubleshooting procedure is carried out by a software program. As each photosensor comprises a photo-detector and an associated light emitter for illuminating the photo-detector, the test is based on the output voltage of the photo-detector in response to a current value on the light emitter. Based on the two or more current values set to the light emitter and the corresponding measured output voltage values, the software program determines whether the photosensor is functional. If the photosensor is not functional, possible causes and suggested remedies are provided to the operator of the machine.

32 Claims, 6 Drawing Sheets

METHOD AND APPARATUS FOR TROUBLESHOOTING PHOTOSENSORS

FIELD OF THE INVENTION

The present invention relates generally to checking photosensors and, more particularly, to troubleshooting a large number of photosensors in a machine automatically.

BACKGROUND OF THE INVENTION

Photosensors are commonly used in a mail-related machine to make sure all parts in the machine function in a coordinated way. For example, in a mail stacker, photosensors can be used to monitor the arrival of a mailpiece so that a certain roller can start to move in order to bring that mailpiece into a mail stack. Photosensors can also be used in the same machine to monitor the size of the growing mail stack so as to notify an operator when to take the mail stack off the mail stacker. In a mail inserting machine where a plurality of enclosure feeders are used to release documents onto the machine chassis and the released documents are pushed into a stack to be inserted into an envelope, photosensors can be used to check the arrival of the envelope, the movement of the released documents and so forth.

Figure 1A:
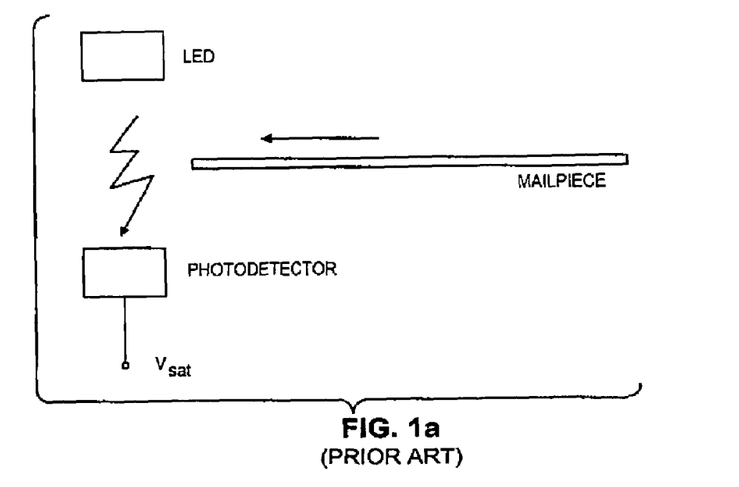
FIG. 1a is a schematic representation illustrating a photosensor being used to detect the arrival of a mailpiece.
Figure 1B:
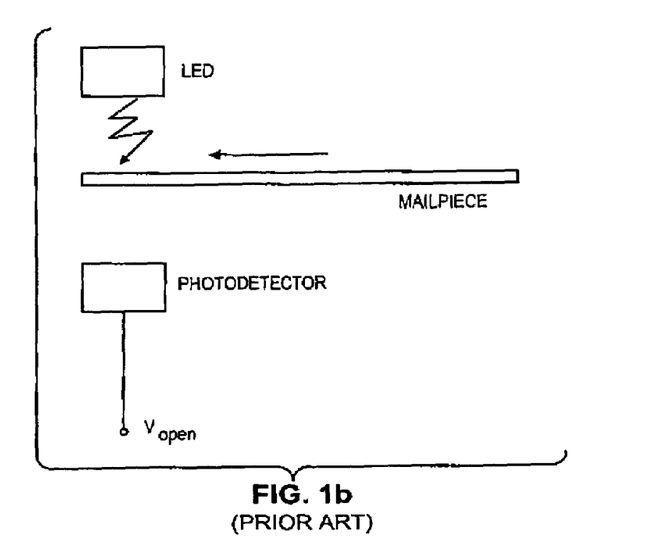
FIG. 1b is a schematic representation illustrating the photo-detector of the photosensor being blocked by the arriving mailpiece.

A photosensor, in general, comprises a photo-detector and a light-emitting diode (LED). When the photosensor is active, the LED is activated to produce light to illuminate the photo-detector, as illustrated in FIG. 1a. When the photo-detector is not blocked, the illumination causes the photo-detector to become saturated. In this state, the output voltage of the photo-detector circuit is generally low. But when the photo-detector is blocked by an object coming into the space between the LED and the photo-detector as illustrated in FIG. 1b, the photo-detector is in a high resistive state and the output voltage of the photo-detector circuit is generally high or substantially equal to the supply voltage. The photsensors are used not only to detect the incoming mail pieces, but also pieces leaving the sensor.

Figure 2:
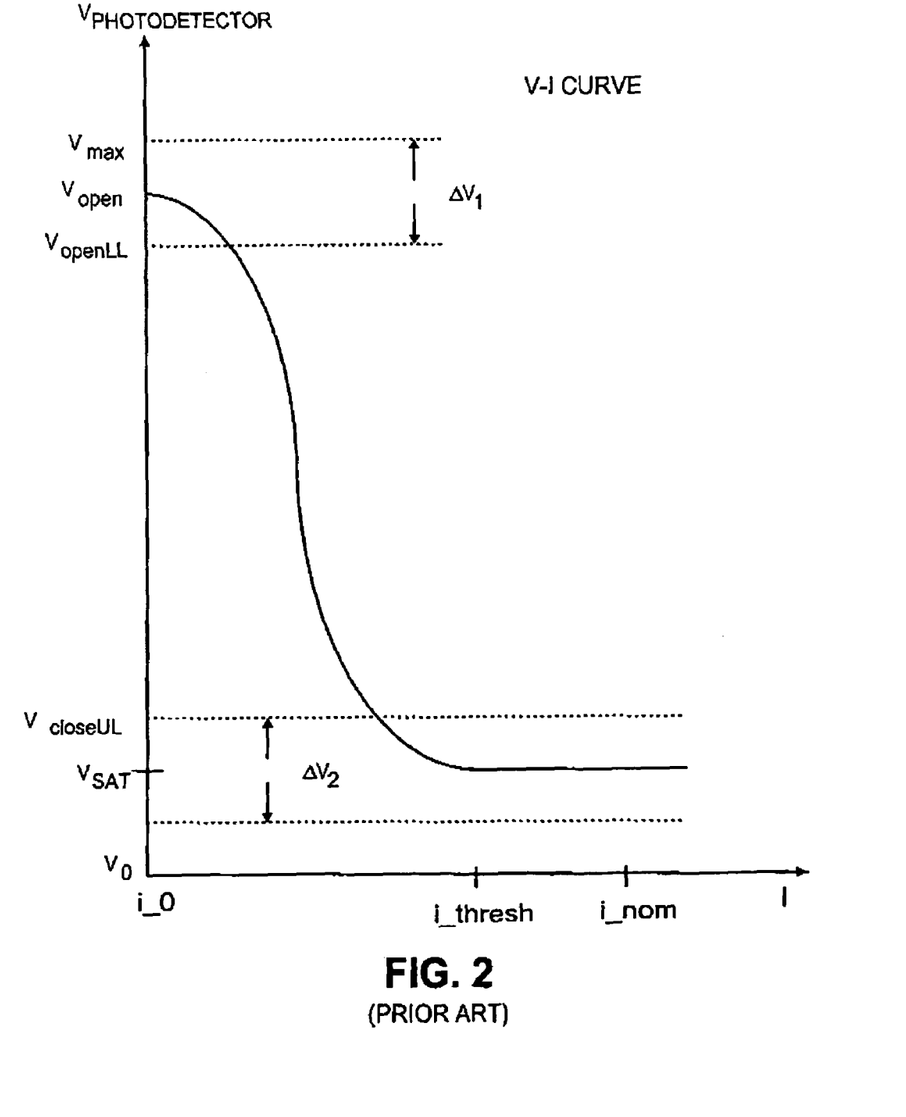
FIG. 2 is a plot showing a typical relationship between the output voltage of the photo-detector and the supply current to the light source.

A plot of the output voltage of a typical photo-detector versus the supply current to the LED (V-I Curve) is shown in FIG. 2. As shown in FIG. 2, the photo-detector becomes saturated at $i_{LED}=i\_thresh$. In general, the output voltage of a photo-detector depends on the light output of the LED, the distance of the photo-detector from the LED, the alignment between the photo-detector and the LED, and so forth. In order to ensure that the photo-detector is saturated when it is not blocked, the supply current to the LED is usually set to a value that is higher than $i\_thresh$. For example, the supply current on the LED can be set at $i\_nom$, as shown in FIG. 2. Preferably, $i\_nom$ is greater than $i\_thresh$, as shown in FIG. 2, however, for testing purposes $i\_nom$ may be selected to be the same as $i\_thresh$.

In the past, troubleshooting of photosensors relies on manual testing where the photo-detector is manually blocked and unblocked while the LED is on, and the output voltage of photo-detector is measured using a multi-meter, for example. This manual testing method is cumbersome and sometime impractical. For example, some photosensors in a mailing machine may be located deep inside the machine. Accessing those photosensors may be very difficult.

Thus, it is advantageous and desirable to provide a method and system for testing one or more photosensors in a mailing machine in a systematic and automatic fashion.

SUMMARY OF THE INVENTION

It is a primary object of the present invention to provide a method and apparatus to carry out an automated procedure for troubleshooting a plurality of photosensors in a machine in a systematic fashion. This object can be achieved by using a software program to analyze the output voltage of a photo-detector in response to a current setting in the associated light emitter.

Thus, it is the first aspect of the present invention to provide a method for determining whether a photosensor in an apparatus is operational, the photosensor comprising a light emitter and a light detector, wherein when the photosensor is operational, the light emitter is capable of producing light for illuminating the light detector in response to a current applied to the light emitter; and the light detector has an output voltage indicative of the applied current to the light emitter, wherein the output voltage of the light detector falls in a first predetermined voltage range ($\Delta V1$) when the applied current is substantially equal to a first current value ($I\_0$); and the output voltage of the light detector falls in a second predetermined voltage range ($\Delta V2$) lower than the first predetermined voltage range when the applied current is substantially equal to a second current value ($I\_nom$), and wherein the apparatus comprises:

a control module, adapted to provide a data signal indicative of the output voltage of the light detector. The method comprises the steps of:

conveying a request signal to the control module for causing the control module to provide the data signal;

measuring the output voltage of the light detector based on the data signal, when the applied current is set to one of the first and second current values, for obtaining a measured voltage value, and determining whether the measured voltage value falls in the corresponding predetermined voltage range, thereby indicating that the photosensor is operational.

The control module is capable of changing the applied current, and the method further comprises the steps of:

conveying a further request signal to the control module for causing the control module to change the applied current from said one of the first and second current values to another of the first and second current values and for causing the control module to provide the data signal after the applied current has changed;

measuring the output voltage of the light detector for obtaining a further measured voltage value; and determining whether the further measured voltage falls in the other corresponding predetermined voltage range, thereby indicating that the photosensor is operational.

When the current value is set to the first current value, and the measured voltage value is lower than the first determined voltage range, the method further comprises the step of:

providing a warning signal indicating that the photosensor is non-operational in that the light detector may be defective.

When the current value is set to the second current value, and the measured voltage value is higher than the first determined voltage range, the method further comprises the step of:

providing a warning signal indicating that the photosensor is non-operational in that:

the light produced by the light emitter insufficiently illuminates the light detector, or the light produced by the light emitter is at least partially blocked by an unwanted light-absorbing material layer on the light detector, or the light produced by the light emitter is at least partially blocked by an unwanted obstruction in the light path, or the light detector and the light emitter are misaligned such that only an insignificant portion of the light produced by the light emitter illuminates the light detector.

According to the present invention, the control module is operatively connected to a troubleshooting device comprising a software program, and wherein at least the conveying step and the determining step are carried out by the software program.

Another aspect of the present invention to provides a photosensor troubleshooting system for use with an apparatus comprising at least a photosensor, the photosensor comprising a light emitter and a light detector, wherein when the photosensor is operational, the light emitter is capable of producing light for illuminating the light detector in response to a current applied to the light emitter; and the light detector has an output voltage indicative of the applied current to the light emitter, wherein the output voltage of the light detector falls in a first predetermined voltage range ($\Delta V1$) when the applied current is substantially equal to a first current value (I_0); and the output voltage of the light detector falls in a second predetermined voltage range ($\Delta V2$) lower than the first predetermined voltage range when the applied current is substantially equal to a second current value (I_nom), and wherein the apparatus comprises:

a control module, adapted to provide a data signal indicative of the output voltage of the light detector. The troubleshooting system comprises:

means, operatively connected to the control module, for conveying a request signal to the control module in order to cause the control module to provide the data signal when the applied current is set to one of the first and second current values, means, response to the data signal, for obtaining the output voltage of the light detector based on the data signal so as to determine whether the obtained voltage value falls in the corresponding predetermined voltage range.

The system further comprises a software program for providing the request signal and for carrying out said determining.

According to the present invention, the control module is capable of changing the applied current, and wherein the conveying means is capable of conveying a further request signal to the control module for causing the control module to change the applied current from said one of the first and second current values to another of the first and second current values and for causing the control module to provide a further data signal indicative of the output voltage of the light detector after the applied current on the light emitter has changed; and the obtaining means is adapted to further obtain the output voltage of the light detector based on the further data signal so as to determine whether the further obtained voltage falls in the other corresponding predetermined voltage range.

Advantageously, the system further comprises a warning module for indicating whether the photosensor is operational based on said determining. When the photosensor is non-operational, said warning module is adapted to indicate at least one possible cause as to why the photosensor is non-operational based on said determining.

The present invention will become apparent upon reading the description taken in conjunction with FIGS. 2 to 5b.

BEST MODE FOR CARRYING OUT THE INVENTION

Figure 3:
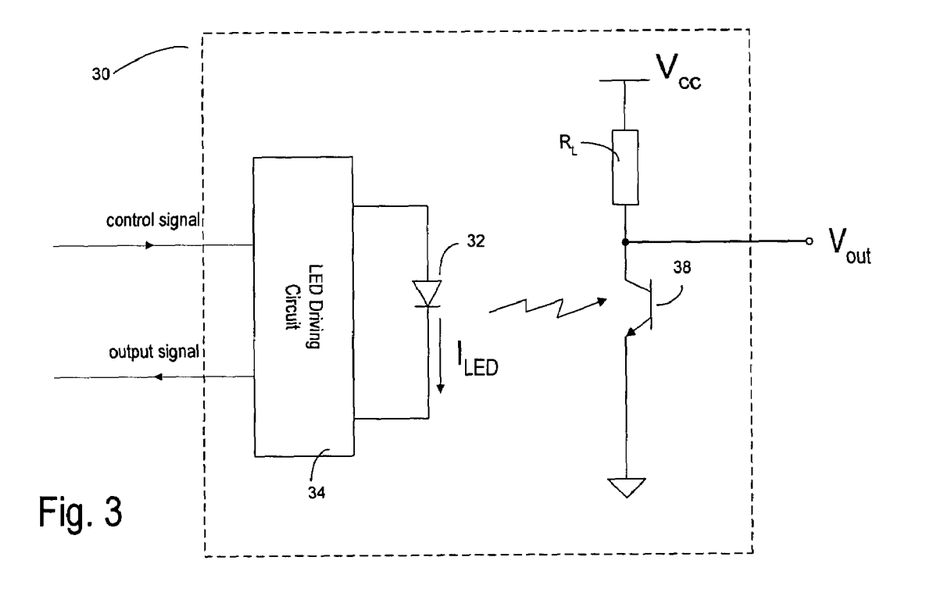
FIG. 3 is a schematic representation illustrating a photosensor and its related signals.

The photosensor troubleshooting method and system, according to the present invention, are based on the output voltage of a photo-detector in response to the supply current to the light source that illuminates the photo-detectors. As shown in FIG. 3, the photosensor 30 comprises a light source, such as light-emitting diode (LED) 32 driven by a driving circuit 34, and a photo-detector 38. The supply current $i_{LED}$ on the LED 32 is controllable by a control signal. For example, the supply current $i_{LED}$ can be set to zero (i_0), i_nom (see the V-I Curve of FIG. 2) or a current value between these two values. The output voltage (Vout) of the photo-detector 38 corresponding to the current setting can be measured for troubleshooting purposes. When the supply current $i_{LED}$ can be set to i_0, there will be no light output from the LED 32. This setting is substantially equivalent to the situation when the photo-detector 38 is blocked by a mailpiece (see FIG. 1b) or any object moving the space between the LED 32 and the photo-detector 38. As such, it is not necessary to physically block the photo-detector with an object in order to check out whether the photosensor 30 is functional. Preferably, an output signal from the driving circuit 34 is provided so that the supply current $i_{LED}$ can be measured if it is necessary to check out whether the LED is functional.

Figure 4:
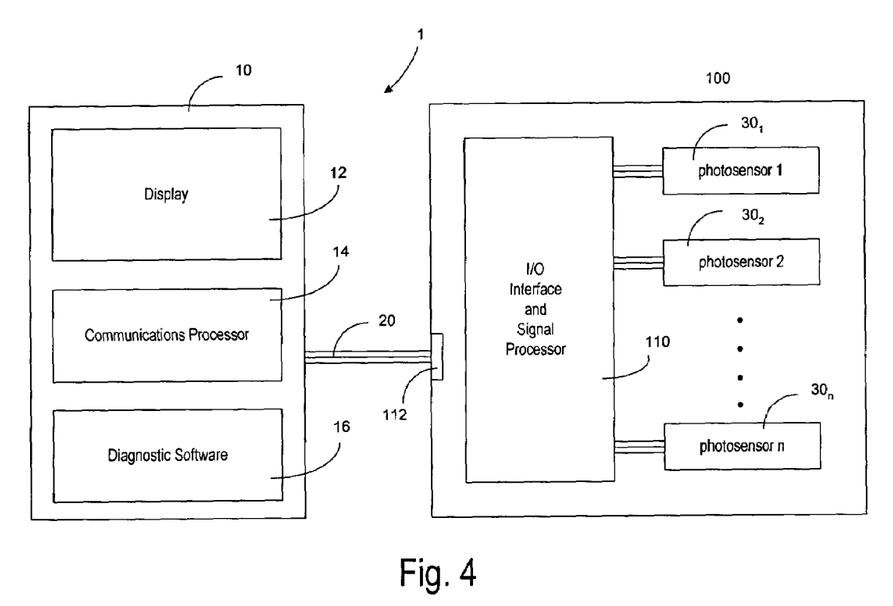
FIG. 4 is a schematic representation illustrating a system for troubleshooting a plurality of photosensors in a machine, according to the present invention.

In a machine where a plurality of photosensors are used for detection and monitoring purposes, the machine usually has a control module for controlling those photosensors. As shown in FIG. 4, the machine 100 has a control module 110 operatively connected to plurality of photosensors $30_1$, $30_2$, ..., $30_n$. The control module 110 can be used to selectively send a control signal to any of the photosensors $30_1$, $30_2$, ..., $30_n$ to set a current value to the LED of a selected photosensor. Furthermore, the control module 110 includes a signal processor to measure the output voltage Vout and the supply current $i_{LED}$ of any one of the photosensors. The control module 110 further includes an I/O interface so as to allow an external troubleshooting module 10, which is connected through a connector cable 20 to the control module 110, to selectively check out whether any of the photosensors $30_1$, $30_2$, ..., $30_n$ functions properly. For example, the connection between the control module 110 and the troubleshooting module 10 can be carried out through a serial I/O port 112 of the control module 110. It should be noted that the control module 110 may have a plurality of circuit boards, each board having a plurality of control circuits to control a plurality of photosensors. The circuit boards can be logically represented as nodes and the individual photosensors can be selected through the addresses on the nodes.

According to the preferred embodiment of the present invention, the troubleshooting module 10 comprises a display 12, a communications processor 14 and a diagnostic software program 16. The diagnostic software program 16 is designed such that one or more of the photosensors $30_1$, $30_2$, ..., $30_n$ can be selected to be diagnosed on demand, or one or more of the photosensors $30_1$, $30_2$, ..., $30_n$ can be diagnosed automatically at power-up. The diagnosis result is then displayed on the display 12 to allow an operator to find out whether the photosensors are functional. Moreover, it is preferred that the diagnostic software program is designed to provide the possible causes to the operator when the software program determines that one or more photosensors do not function normally (see Table I). The communications process 14 is used to enable the exchange of signals between the control module 110 and the diagnostic module 10. For example, if the operator wants to diagnose a certain photosensor 30, the operator can use a mouse or the like to select that photosensor. Alternatively, the operator may press a button to run health check on all the sensors of a given node. The communications processor 14, in response to that selection, sends a request signal through the cable 20 to the control module 110.

Based on the request signal, the control module 110 sends a control signal to the selected photosensor in order to set a current value $i_{LED}$, and obtains the output voltage Vout of the selected photosensor. Also through the cable 20, the communications processor 14 obtains the output voltage and the supply current of the selected photosensor and put these values on the display 12. At the same time, the communications processor 14 sends the obtained values to the diagnostic software for diagnostic purposes.

If a photosensor 30 functions normally, the output voltage of the photo-detector 38 of that photosensor 30 should be in response to the supply current of the respective LED 32, according to the V-I curve of FIG. 2. For example, if the supply current to the LED 32 is set to i_0 (zero), then the output voltage of the photo-detector 38 should be equal to Vopen. Similarly, if the supply current to the LED is set to i_nom, then the output voltage should be equal to Vsat. However, because the output voltage varies with the illumination, which varies with the distance and the alignment between the photo-detector and the LED, it is expected that the measured output voltage falls within a certain voltage range, $\Delta V_2$, as illustrated in FIG. 2, when the supply current is set to i_nom. For example, the output voltage can be greater than the saturation voltage, or Vsat, of the photo-detector. Furthermore, the output voltage of the photo-detector, when the supply current is set to i_0, can vary within a certain voltage range, $\Delta V_1$, because of the variation in the supply voltage Vcc and the load resistor $R_L$ (see FIG. 3). Thus, the output voltage at this state is allowed to vary from $V_{max}$ (maximum value of Vcc, for example) and $V_{openLL}$ (the lower limit of $V_{open}$). Accordingly, the diagnostic software program is design to take into consideration these output voltage variations.

When the output voltage of a photo-detector does not fall within $\Delta V_1$ and $\Delta V_2$, it can be safely assumed that the photosensor does not function properly. There are many possible causes for malfunction. The possible causes can be: (1) a defective photo-detector and/or LED, (2) dirty photo-detector and/or the LED (the surface of the device is coated with an unwanted light-absorbing material, resulting insufficient illumination to the photo-detector), (3) gross misalignment between the LED and the photo-detector, resulting insufficient illumination to the photo-detector, (4) defective wiring in the photo-detector circuit and/or the LED circuit, (5) defective power supply to the photo-detector, and (6) obstruction between the photo-detector and the LED. It is advantageous to provide a diagnostic software program that can automatically carry out a series of test procedures and then provide the possible causes to the operator.

It should be noted that, switches are also used in a mail-related machine to monitor the movement of mailpieces or certain mechanical parts. For example, in a mail stacking machine, it is useful to use a switch to monitor the growth of a mail stack such that when a mail stack reaches a certain length or height, the switch is tripped and the operator is notified. It is advantageous to design the switch circuit such that the output voltage of the switch also falls within $\Delta V_1$ and $\Delta V_2$ when the switch functions normally. Preferably the switch voltage does not fall between $V_{openLL}$ and $V_{closeUL}$ during normal operation. As such, the diagnostic software program can be used to monitor the health of both the switches and the photosensors in the same machine.

Figure 5A:
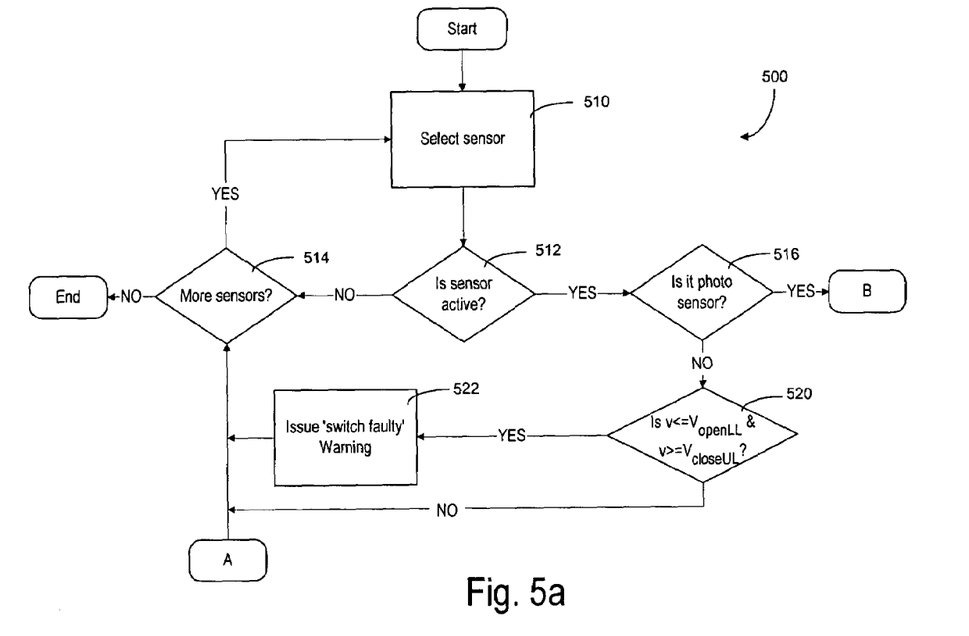
FIG. 5a is one part of the flowchart showing the photosensor troubleshooting algorithm, according to the present invention.
Figure 5B:
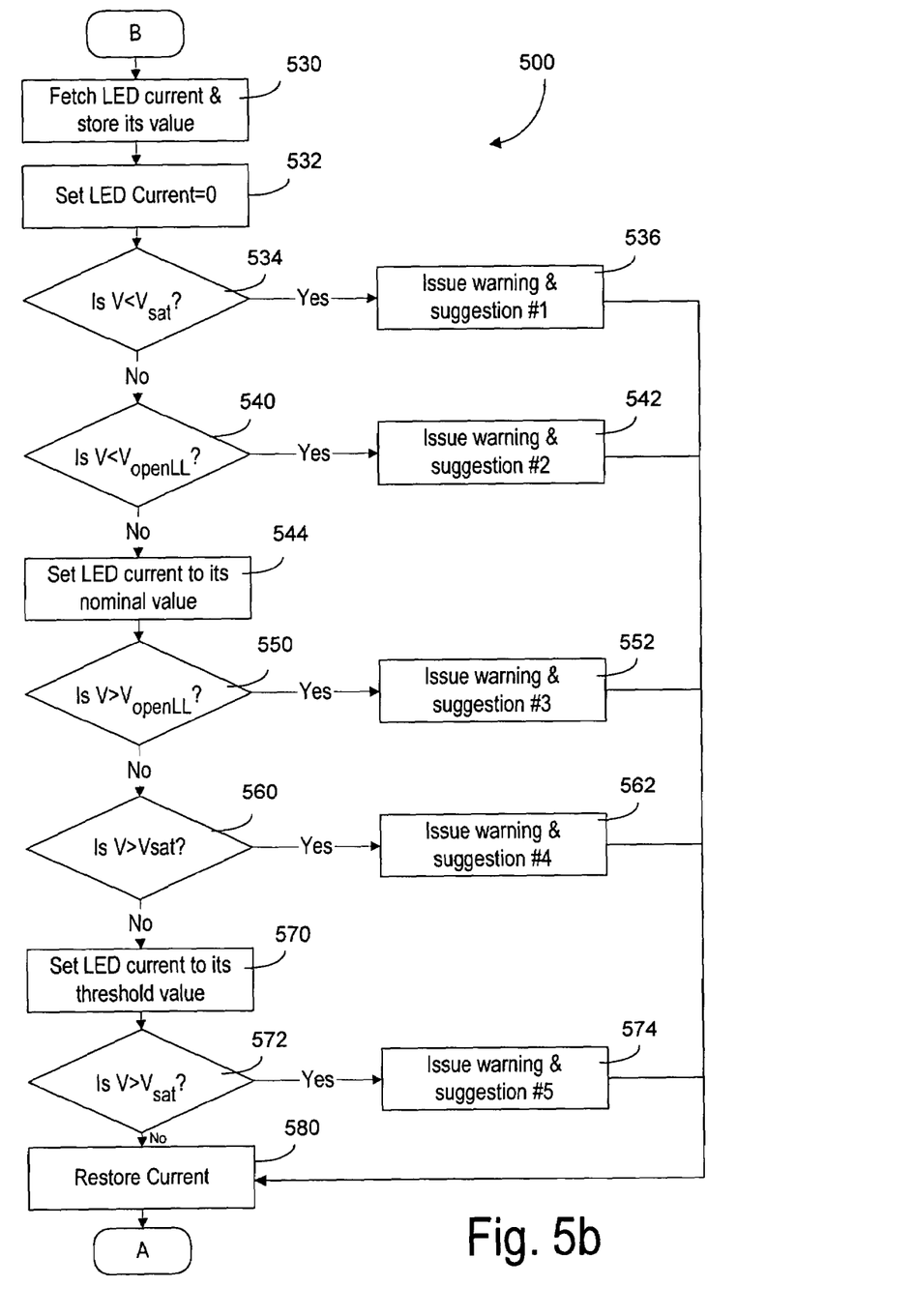
FIG. 5b is another part of the flowchart showing the photosensor troubleshooting algorithm.

FIGS. 5a and 5b show an exemplary diagnostic procedure for photosensor/switch troubleshooting, according to the present invention. As shown in the flowchart 500, a sensor is selected at step 510 from the start of the diagnostic procedure. If the sensor is currently inactive, then a new sensor is selected in the next step if it is determined at step 514 that there are more sensors to be tested. If it is determined at step 512 that the sensor is active, then it is further determined at step 516 whether the sensor is a photosensor or a switch. It should be noted that the diagnostic software program 16 of the present invention has an object model tree, which is configured such that when the algorithm walks down the tree for a particular node in the control module 110, it inquires whether a particular input is connected and whether the selected sensor belongs to a "photosensor" class or a "switch" class. As such, the algorithm can determine whether the input is active or inactive.

If the selected sensor is a switch, it is determined at step 520 whether the switch is non functional. A warning is displayed at step 522 if it is non functional. If the selected sensor is photosensor, the testing procedure starts at step 530, as shown in FIG. 5b.

It is preferred that, prior to testing a photosensor, the value of the supply current to the LED is recorded at step 530 so that the original state of the photosensor can be restored after testing is completed (see step 580).

The testing procedure of a photosensor starts at step 532 where the supply current $i_{LED}$ is set to zero or i_0. If the photosensor is functional, the output voltage of the corresponding photo-detector should be equal to $V_{open}$ and should fall within the first voltage range, $\Delta V_1$ because no light is provided by the LED (see FIG. 2). If the output voltage is smaller then $V_{sat}$, as determined at step 534, then the photosensor is not functional normally. The possible causes would be (a) improper wiring on the photo-detector circuit, (b) a defective power supply, or (c) a defective photo-detector. Accordingly, the software program gives the operator a warning and a list of suggested remedies as to how the problems can be solved, at step 536. Preferably, the warning and suggestion is displayed on the display 12 of the troubleshooting module 10.

If the voltage output as determined at step 540 is higher than $V_{sat}$ but below the first voltage range, $\Delta V_1$, i.e., $V_{openLL}$, this suggests that the photo-detector is picking up extraneous signals. Accordingly, a warning and a suggestion are displayed at step 542.

If the output voltage falls within the range $\Delta V_1$, the value of supply current to the LED is set to i_nom at step 544. At this current setting, the output voltage from the photo-detector should be within the second voltage range, $\Delta V_2$ because the photo-detector is expected to be fully illuminated and, therefore, saturated. However, if the output voltage is high, it is possible that (a) the photo-detector is blocked or that (b) the photo-detector and the LED are grossly misaligned. Thus, if it is determined at step 550 that the output voltage is very high, a corresponding warning and suggestion is given to the operator at step 552.

If the output voltage is somewhere between the first voltage range, $\Delta V_1$, and the second voltage range, $\Delta V_2$, then the photo-detector is not fully saturated. It is very likely that (a) the photo-detector or the LED is dirty, or (b) the alignment between the photo-detector and the LED is slightly off. Thus, if it is determined at step 560 that the photo-detector is not fully saturated, a warning and suggestion is given to the operator at step 562.

In general, if the output voltage of the photo-detector falls within the second voltage range, $\Delta V_2$, when the current is set to i_nom, it is most likely that the photosensor is functional. Nevertheless, it is advantageous to take one more test procedure on the photosensor to determine whether the photosensor is close to failure. In order to carry out the last test, the supply current to the LED is set to i_thresh at step 570. At this current setting, the output voltage is still expected to be within the second voltage range. If not, a warning and suggestion is displayed in the display 12 of the diagnostic module 10. However, if it is determined at step 572 that the selected photosensor is functional, then the original LED current setting is restored at step 580. Current may also be restored even when errors are detected. A new photosensor is selected for testing until all photosensors are tested.

The warnings and suggestions that the software program provides to the operators in different voltage/current situations are summarized in Table I. In addition to information listed in Table I, the operator may further be provided with measured current and voltage values to assist in the error analysis.

TABLE I

| Test | Error Conditions | Information | Suggestion |
|---|---|---|---|
| 1. | V < Vsat @ I_0 | Possible causes:<br>A) Detector wiring problems.<br>B) Power supply problems.<br>C) Bad detector. | Verify detector voltage changes with light:<br>Using a flashlight, verify the detector voltage changes with light.<br>If no change, check detector wiring.<br>If still no change, replace the detector.<br>Verify correct power supply voltage.<br>If condition persists, replace the detector. |
| 2. | V < VopenLL @ I_0 | Sensor detecting extraneous signals.<br>Possible causes:<br>A) Detector wiring problems.<br>B) Power supply problems.<br>C) Bad detector. | Check the detector wiring for loose connectors.<br>Verify correct power supply voltage.<br>If condition persists, replace the detector. |
| 3. | V > VopenLL @ I_nom | Sensor appears BLOCKED.<br>Possible causes:<br>A) Obstruction between the LED and the detector.<br>B) Gross misalignment of LED and detector.<br>C) LED does not produce light due to wiring problems or bad LED.<br>D) Detector wiring problems or bad detector. | Clear any obstructions.<br>Verify sensors are properly aligned.<br>Verify LED produces light:<br>Use IR test strip.<br>If no light, check LED wiring.<br>If still no light, replace LED.<br>Verify detector voltage changes with light:<br>Using a flashlight, verify the detector voltage changes with light.<br>If no change, check detector wiring.<br>If still no change, replace the detector. |
| 4. | V > Vsat @ I_Nom. | Sensor not fully saturated.<br>Possible causes:<br>A) Dirty photocells<br>B) Misalignment of LED and detector. | Clean photocells.<br>Verify sensors are properly aligned. |
| 5. | V > Vsat @ I_thresh | Sensor close to failure.<br>Possible causes:<br>A) Dirty photocells<br>B) Misalignment of LED and detector. | Clean photocells.<br>Verify sensors are properly aligned. |
| 6. | If all voltages at I_0, I_threshold and I_nom are within | The photocell health check ran successfully. If the photocell health check was run after a photocell problem was reported then the problem might be | Inspect wiring for loose connectors.<br>Verify sensors are properly aligned and that mounting brackets are secure. |

TABLE I-continued

| Test | Error Conditions | Information | Suggestion |
|---|---|---|---|
| | tolerance range and photocell problems were reported | intermittent due to vibrations or loose connectors | |

Although the invention has been described with respect to a preferred embodiment thereof, it will be understood by those skilled in the art that the foregoing and various other changes, omissions and deviations in the form and detail thereof may be made without departing from the scope of this invention.

What is claimed is:

1. A method for automatically determining whether a photosensor in an apparatus is operational, the photosensor comprising a light emitter and a light detector, wherein when the photosensor is operational, the light emitter is capable of producing light for illuminating the light detector in response to a current applied to the light emitter; and the light detector has an output voltage indicative of the applied current to the light emitter, wherein the output voltage of the light detector falls in a first predetermined voltage range ($\Delta V1$) when the applied current is substantially equal to a first current value (I_0); and the output voltage of the light detector fails in a second predetermined voltage range ($\Delta V2$) lower than the first predetermined voltage range when the applied current is substantially equal to a second current value, (I_nom), and wherein the apparatus comprises:

a control module, adapted to provide a data signal indicative of the output voltage of the light detector, said method comprising the steps of:

conveying a request signal to the control module for causing the control module to provide the data signal;

measuring the output voltage of the light detector based on the data signal, when the applied current is set to one of the first and second current values, for obtaining a measured voltage value, and determining whether the measured voltage value falls in the corresponding predetermined voltage range, thereby indicating that the photosensor is operational.

2. The method of claim 1, wherein the control module is capable of changing the applied current said method further comprising the steps of:

conveying a further request signal to the control module for causing the control module to change the applied current from said one of the first and second current values to another of the first and second current values and for causing the control module to provide the data signal after the applied current has changed;

measuring the output voltage of the light detector based on the data signal for obtaining a further measured voltage value; and determining whether the further measured voltage falls in the other corresponding predetermined voltage range, thereby indicating that the photosensor is operational.

3. The method of claim 1, said one of the first and second current values is the first current value, and the measured voltage value is lower than the first determined voltage range, said method further comprising the step of:

providing a warning signal indicating that the photosensor is non-operational.

4. The method of claim 3, wherein the provided warning signal indicates that the light detector is defective.

5. The method of claim 1, wherein said one of the first and second current values is the second current value, and the measured voltage value is higher than the second determined voltage range, said method further comprising the step of:

providing a warning signal indicating that the photosensor is non-operational.

6. The method of claim 5, wherein the provided warning signal indicates that the light produced by the light emitter insufficiently illuminates the light detector.

7. The method of claim 5, wherein the provided warning signal indicates that the light produced by the light emitter is at least partially blocked by an unwanted light-absorbing material layer on the light detector.

8. The method of claim 5, wherein the provided warning signal indicates that the light emitter and the light detector are misaligned such that only an insignificant portion of the light produced by the light emitter illuminates the light detector.

9. The method of claim 2, wherein said one of the first and second current values is the first current value, the other of the first and second current values is the second current value, the measured voltage falls in the first predetermined voltage range, and the further measured voltage value is higher than the first predetermined voltage range, said method further comprising the step of:

providing a warning signal indicative that the photosensor is non-operational.

10. The method of claim 9, wherein the provided warning signal indicates that the light produced by the light emitter insufficiently illuminates the light detector.

11. The method of claim 9, wherein the provided warning signal indicates that the light produced by the light emitter is at least partially obstructed.

12. The method of claim 9, wherein the provided warning signal indicates that the light emitter and the light detector are misaligned such that only an insignificant portion of the light produced by the light emitter illuminates the light detector.

13. The method of claim 1, wherein the apparatus further having at least one further photosensor, and the control module is capable of providing information for determining whether the further photosensor is operational, said method comprising the step of:

conveying a further request signal for causing the control module to provide a further data signal indicative of the information.

14. The method of claim 1, wherein the control module is operatively connected to a troubleshooting device comprising a software program, and wherein at least the conveying step and the determining step are carried out by the software program.

15. The method of claim 1, wherein a saturation voltage represents a minimum voltage across the light detector when illuminated, and a third current to the light emitter represents a current at which the light detector normally becomes saturated, and the method further comprises:
   setting the applied current to the third current value;
   measuring the output voltage of the light detector; and
   providing a warning signal if the output voltage is greater than the saturation voltage.

16. The method of claim 15 wherein the warning signal includes an indication that the photosensor may soon become inoperative.

17. The method of claim 1, wherein said one of the first and second current values is the first current value, and the measured voltage value is lower than the second determined voltage range, said method further comprising the step of:
   providing a warning signal indicating that the photosensor may be faulty.

18. The method of claim 1, wherein the output voltage of the light detector falls in the second predetermined voltage range when the applied current is substantially equal to a threshold current value (I_thresh); and further comprising the steps of
   measuring the output voltage of the light detector based on the data signal when the applied current is set to the threshold current value for obtaining the measured voltage value, the threshold current value being less than the second current value, and
   determining whether the measured voltage value falls within the second predetermined voltage range.

19. The method of claim 18, wherein the measured voltage was within the second voltage range when the applied current was set to the second current value, and the measured voltage was greater than the second voltage range when the applied current was set to the threshold current value, said method further comprising the step of:
   providing a warning indication that the photosensor is close to becoming inoperational.

20. A photosensor troubleshooting system for use with an apparatus comprising at least a photosensor, the photosensor comprising a light emitter and a light detector, wherein when the photosensor is operational,
   the light emitter is capable of producing light for illuminating the light detector in response to a current applied to the light emitter; and
   the light detector has an output voltage indicative of the applied current to the light emitter, wherein
   the output voltage of the light detector falls in a first predetermined voltage range (ΔV1) when the applied current is substantially equal to a first current value (I_0); and
   the output voltage of the light detector falls in a second predetermined voltage range (ΔV2) lower than the first predetermined voltage range when the applied current is substantially equal to a second current value (I_nom), and wherein the apparatus comprises:
   a control module, adapted to provide a data signal indicative of the output voltage of the light detector, said troubleshooting system comprising:
   means, operativety connected to the control module, for conveying a request signal to the control module in order to cause the control module to provide the data signal when the applied current is set to one of the first and second current values,
   means, response to the data signal, for obtaining the output voltage of the light detector based on the data signal so as to determine whether the obtained voltage value falls in the corresponding predetermined voltage range.

21. The system of claim 20, further comprising a software program for providing the request signal and for carrying out said determining.

22. The troubleshooting system of claim 20, wherein the control module is capable of changing the applied current, and wherein
   the conveying means is capable of conveying a further request signal to the control module for causing the control module to change the applied current from said one of the first and second current values to another of the first and second current values and for causing the control module to provide a further data signal indicative of the output voltage of the light detector after the applied current on the light emitter has changed; and
   the obtaining means is adapted to further obtain the output voltage of the light detector based on the further data signal so as to determine whether the further obtained voltage falls in the other corresponding predetermined voltage range.

23. The system of claim 22, further comprising a software program for providing the request signal and the further request signal, and for carrying out said determining whether the obtained voitsue value falls in the corresponding predetermined voltage range.

24. The system of claim 20, further comprising a warning module for indicating whether the photosensor is operational based on said determining.

25. The system of claim 24, wherein when the photosensor is non-operational, said warning module is adapted to indicate at least one possible cause as to why the photosensor is non-operational based on said determining whether the obtained voltage value falls in the corresponding predetermined voltage range.

26. The system of claim 24, wherein said one of the first and second current values is the first current value, and the measured voltage value is lower than the first determined voltage range, said warning module is adapted to indicate that the light-detector is defective.

27. The system of claim 24, wherein said one of the first and second current values is the second current value, and the measured voltage value is higher than the first determined voltage range, said warning module is adapted to indicate at least one possible cause including that the light produced by the light emitter insufficiently illuminates the light detector.

28. The system of claim 24, wherein said one of the first and second current values is the second current value, and the measured voltage value is higher than the second determined voltage range, said warning module is adapted to indicate at least one possible cause
   including that the light produced by the light emitter is at least partially blocked by an unwanted light-absorbing material layer on the light detector.

29. The system of claim 24, wherein said one of the first and second current values is the second current value, and the measured voltage value is higher than the second determined voltage range, said warning module is adapted to indicate at least one possible cause
   including that the light emitter and the light detector are misaligned such that only an insignificant portion of the light produced by the light emitter illuminates the light detector.

30. The system of claim 24 wherein said one of the first and second current values is the first current value, and the measured voltage value is lower than the second determined voltage range, said warning module is adapted to indicate at least one possible cause including that the light detector is faulty.

31. The system of claim 20, wherein the output voltage of the light detector falls in the second predetermined voltage range when the applied current is substantially equal to a threshold current value (I_thresh); and wherein
the obtaining means measures the output voltage of the light detector based on the data signal when the applied current is set to the threshold current value for obtaining the measured voltage value, the threshold current value being less than the second current value, and to determine whether the measured voltage value falls within the second predetermined voltage range.

32. The system of claim 31, further comprising a warning module whereby when the measured voltage is within the second voltage range when the applied current is set to the second current value, and the measured voltage is greater than the second voltage range when the applied current is set to the threshold current value, the warning module provides a warning indication that the photosensor is close to becoming inoperational.

* * * * *